United States Patent [19]

Haigh

[11] Patent Number: 5,310,554
[45] Date of Patent: May 10, 1994

[54] HIGH PURITY BETA-CAROTENE

[75] Inventor: W. Geoffrey Haigh, Seattle, Wash.

[73] Assignee: Natural Carotene Corporation, Tukwila, Wash.

[21] Appl. No.: 967,897

[22] Filed: Oct. 27, 1992

[51] Int. Cl.$^5$ .......................... A61K 9/16; A61K 9/48; A61K 9/20; A61K 35/78
[52] U.S. Cl. .................................. 424/439; 424/451; 424/464; 424/489; 424/195.1; 585/825
[58] Field of Search ............... 424/439, 451, 464, 489; 585/825

[56] References Cited

U.S. PATENT DOCUMENTS

| | | | |
|---|---|---|---|
| 3,039,877 | 6/1962 | Borenstein | 99/81 |
| 3,492,202 | 1/1970 | Bohinski | 195/28 |
| 4,199,895 | 4/1980 | Avron et al. | 47/1.4 |
| 4,439,629 | 3/1984 | Rüegg | 585/803 |
| 4,680,314 | 7/1987 | Nonomura | 514/725 |
| 4,713,398 | 12/1987 | Nonomura | 514/725 |
| 4,851,339 | 7/1989 | Hills | 435/67 |
| 5,019,668 | 5/1991 | Keat et al. | 585/864 |
| 5,206,025 | 4/1993 | Courteille et al. | 424/439 |

OTHER PUBLICATIONS

Ben–Amotz et al., "Bioavailability of a Natural Isomer Mixture as Compared with Synthetic all-trans-B-Carotene in Rats and Chicks," *J. Nutr.* 119(7):1013–1019, 1989.

Ben–Amotz, "The Wavelength Dependence of Massive Carotene Synthesis in *Dunaliella bardawil* (Chlorophyceae)," *J. Phycol.* 25:175–178, 1989.

Ben–Amotz et al., "Stereoisomers of B–Carotene and Phytoene in the Alga *Dunaliella bardawil*," *Plant Physiol.* 86:1286–1291, 1988.

O'Neil et al., "Comparison of Liquid Chromatographic Methods for Determination of Cis–Trans Isomers of B–Carotene," *J. Assoc. Off. Anal. Chem.* 74:36–42, 1991.

Burton, "Antioxidant Action of Carotenoids," *J. Nutr.* 119(1):109–111, 1989.

Primary Examiner—Thurman K. Page
Attorney, Agent, or Firm—Seed and Berry

[57] ABSTRACT

Compositions of high-purity natural beta-carotene and of the 9-cis isomer of beta-carotene are provided, as are methods for the production of these compositions from plant matter, conveniently algae such as Dunaliella species. Typically, the compositions contain at least about 5% 9-cis beta-carotene and less than or equal to 40% of all-trans-beta-carotene, and in some cases may contain 75% 9-cis beta-carotene or higher. The compositions are suitable for administration to humans or other animals, particularly for oral delivery, in a variety of formulations and dosages as pharmaceutical agents or as dietary supplements.

26 Claims, 4 Drawing Sheets

HIGH PURITY BETA-CAROTENE

BACKGROUND OF THE INVENTION

The present invention relates generally to compositions of purified natural beta-carotenes and methods for their purification from plants. More particularly, the beta-carotene preparations are enriched in the 9-cis isomer compared to the all-trans isomer. The purified beta-carotenes are useful as dietary vitamin A supplementation, as pharmaceuticals and, particularly preparations containing high purity 9-cis beta-carotene, as anti-oxidants in a variety of therapeutic and preventative applications.

The carotenes are chemical precursors of vitamin A. Vitamin A, which is synthesized from carotenes, is essential to a wide variety of physiologic processes in animals, including humans. For example, vitamin A is important in visual sensitivity, and deficiencies of vitamin A may lead to lack of night vision or even blindness. Vitamin A is also necessary to the proper functioning of epithelial tissues.

The carotenes are composed of several forms, including alpha-, beta- and gamma-carotenes. Of these, the beta-carotene isomers have the most vitamin A activity and are the most prevalent in nature, being found in dark green leafy vegetables, yellow and orange vegetables and fruits, and in algae. The concentration of beta-carotene in the edible plants is relatively low and large quantities must be consumed, or else the beta carotene must be supplied as a dietary supplement.

More recently, beta-carotene has been reported to prevent or reduce the risk of heart disease and stroke and certain types of cancers, such as cancer of the breast, lung, colon, prostate, and cervix.

To meet the growing commercial markets in health and coloring industries, a number of methods have been proposed to purify the beta-carotenes. Few procedures, if any, however, have successfully overcome the considerable obstacles posed by the need to prepare compounds of high purity from natural sources in an economical manner while maintaining acceptability to the consumer and regulatory agencies. For example, U.S. Pat. No. 4,439,629 to Rüegg describes treating algae with calcium hydroxide at an elevated temperature to saponify the chlorophyll and produce a residue which is then filtered, dried, and extracted with a solvent, such as a halogenated hydrocarbon or an aliphatic or aromatic hydrocarbon, and recrystallized to yield enriched all-trans beta carotene.

U.S Pat. No. 5,019,668 to Keat et al., describes the recovery of carotenoids from palm oil by an esterification process using an edible oil and subjecting the mixture to vacuum distillation at a substantially elevated temperature. The concentration of beta-carotene in these preparations was described as being up to about 1.9%.

U.S. Pat. No. 4,680,314 to Nomura et al. describes a process for concentrating algae and extracting beta-carotene with an edible oil such as vegetable oil at elevated temperatures, i.e., 66°–100° C. The concentration of carotene in the oil extract was reported to be on the order of 1.9%. U.S. Pat. No. 4,713,398, also to Nomura et al., describes compositions of carotene prepared from algae at concentrations of 0.5% to 7.5% by weight of an edible-oil medium.

Beta-carotene has been prepared by chemical synthesis, but results in the production of only the all-trans form and very little of the cis-isomers of beta-carotene.

There remains a significant need in the art for a method of producing natural beta-carotene compositions of high purity, particularly compositions which are enriched in the 9-cis isomer of beta carotene. The method desirably will provide beta-carotene in a form which maintains its anti-oxidant capability, and in a form which is acceptable to food and health regulatory agencies and to consumers. Moreover, the methods should provide the ability to produce the beta-carotene containing compositions on a large scale and in an economically feasible manner. Quite surprisingly, the present invention fulfills these and other related needs.

SUMMARY OF THE INVENTION

The present invention provides compositions of natural high-purity beta-carotene and of the 9-cis isomer of beta carotene, and methods for their production from plant matter. Thus, in one embodiment the invention comprises substantially purified, naturally-occurring beta-carotene isomers, in relative amounts of at least 40% 9-cis beta-carotene and less than about 50% all-trans beta-carotene, more typically comprising at least about 50% 9-cis beta-carotene and less than or equal to 40% of all-trans-beta-carotene. The amount of alpha-carotene in these preparations usually is less than about 10% of the total amount of carotene present. As the preparations are derived from a natural source, conveniently algae such as Dunaliella species, the compositions may further comprise other carotenoids (generally about 2% or less) and other cis-beta carotene isomers (generally about 3% or less). The compositions are substantially free of organic solvent and thus are suitable for administration to humans or other animals.

In other embodiments the compositions, including pharmaceutical compositions, provided by the invention comprise at least about 60% 9-cis beta-carotene and less than or equal to 25% all-trans beta-carotene, and in some cases the beta-carotene may be 75% 9-cis beta-carotene or higher. Formulations of high purity 9-cis beta-carotene are particularly useful for oral delivery.

The high purity natural beta-carotene preparations may be combined with pharmaceutically acceptable carriers, preservatives, vitamin supplements or other medicinal agents in a variety of formulations and dosages for administration to humans or other animals, such as livestock, as pharmaceutical agents or as dietary supplements. The formulation are typically a capsule, liquid, tablet or powder.

In yet other aspects the invention provides convenient and economical methods for purifying beta-carotene, including the 9-cis isomer of beta-carotene, from plants. Plant material, such as algae, is extracted with a solvent or mixture of solvents, typically an organic solvent such as hexane, petroleum ether, cyclohexane, ethyl acetate, ethanol, etc. to produce a crude mixture of carotenes. The solvent is removed from the extract and the extract is then redissolved in a non-polar solvent such as hexane, petroleum ether, cyclohexane, etc. and chromatographed on a column of deactivated alumina. Fractions containing the purified beta-carotene are then collected from the column.

To produce high-purity 9-cis isomer of beta carotene, in one method the high-purity natural beta-carotene collected from the column is further processed. Typically the purified beta-carotene is dissolved in a non-polar solvent at about 35–55° C. to form a saturated solution, which is then chilled to crystallize out the all-trans beta-carotene portion. The solvent is then removed from the supernatant solution to yield a preparation substantially enriched in 9-cis beta-carotene. The procedure may be repeated, i.e., the steps of dissolving in warm non-polar solvent, chilling to crystallize the all-trans beta-carotene, separating the solution from the crystals, and removing the solvent to yield a preparation further enriched in 9-cis beta-carotene.

DESCRIPTION OF THE SPECIFIC EMBODIMENTS

The present invention provides methods for the preparation of highly purified natural beta-carotene and compositions containing the high purity natural beta-carotene. The methods generally involve the separation of the beta-carotene from the neutral and polar lipids of the crude plant extract and removal of oxygen-containing carotenoids.

Also provided are methods for the preparation of and compositions of natural high purity 9-cis isomer of beta-carotene. The compositions may be formulated and used in a number of ways, including, among others, as dietary supplements for humans and other animals, and in the prevention and treatment of certain neoplastic conditions.

The beta-carotene containing compositions of the invention may be prepared from a variety of plant materials, such as algae, palms, vegetables such as spinach, broccoli, alfalfa, and other plants. This method may also be used to purify all-trans isomer from carrots and sweet potatoes, etc. Preferably the plants are algae. Among the algae, preferred classes are Chlorophyta (green algae), of which the preferred genus is Dunaliella. Other genera may be used so long as carotene can be produced in relatively large quantities. Cultivation techniques may significantly increase the amount of carotene present in each algal cell.

Typically, the algae are raised in shallow tanks, bioreactors, man-made or natural ponds at a wide range of temperatures, e.g., from 15–50° C., more preferably about 25–45° C. Preferably the culture medium is salt water, but fresh water can also be used. Fresh water may be made saline by the addition of salt as a culture medium. The medium may be supplemented by the addition of nitrate, phosphate, bicarbonate, iron and trace minerals. Protocols for the large scale propagation of algae are described in, for example, A. Richmond, *Handbook of Microaloal Mass Culture*, CRC Press, Boca Raton, Fla., (1986), which is incorporated herein by reference. When the algal culture reaches the desired density, e.g., about 0.25 to 0.5 grams dry weight/liter, as determined by absorbance, the algae are harvested from the tank or pond by pumping out the water slurry containing the dispersed algae. The slurry may be passed through screens which are sufficiently coarse to allow algae through but which remove larger unwanted objects.

The slurry is then concentrated in algal content, typically by evaporation, centrifugation, flocculation, ultrafiltration, flotation, etc. to allow removal of unnecessary water. In one embodiment, following concentration of the slurry the salt is largely removed by addition of fresh hot water and ultrafiltration. This also breaks the algal cells, liberating the beta-carotene. The concentrate is then centrifuged in a suitable continuous flow centrifuge, such as a cream separator, to yield an upper (cream) phase of carotene and lipid, which is continually removed. This is dissolved in a suitable solvent, such as hexane, cyclohexane, petroleum ether, etc. as described below.

In another embodiment, the algal material is dewatered by centrifugation, ultrafiltration, etc., and the carotenes are then extracted from the algal or other plant preparation by use of a suitable organic solvent. The extraction and subsequent purification procedures are typically performed under low light intensity and under vacuum or an atmosphere of inert gas (e.g., nitrogen) to maximize recovery of non-oxidized carotenes. The extraction solvent or solvent mixture may be organic, such as hexane, hexanes, pentane, heptane, octane, petroleum ethers, cyclohexane, ethyl acetate, acetone, or ethyl alcohol, or inorganic, such as, for example, carbon dioxide as a liquid or as a super-critical fluid.

The solvent is then removed from the crude extract, typically by evaporating under vacuum, and the crude extract is dissolved in a minimum amount of a suitable non-polar solvent, such as hexane, petroleum ethers, cyclohexane, etc.

The solution of extracted and re-dissolved carotene is then applied to a chromatographic column of alumina, preferably alumina which has been deactivated (partially or totally), or silicic acid, FLORISIL ® (magnesium silicate) or the like. The alumina is deactivated by suspending it in aqueous ethanol (ethyl alcohol:water at 70:30 v/v) or similar procedure. The alumina is then packed into the column as a water/alcohol slurry. The column is typically washed to remove the water, such as with ethanol, then with an ethanol/hexane mixture, e.g., 40% ethanol:60% hexane. Several column volumes of a suitable non-polar solvent, e.g., hexane, petroleum ethers, etc. followed by additional washes, typically at least about five to six column volumes, of a 100% non-polar solvent, such as hexane, pentane, heptane, octane, petroleum ethers, etc., but preferably hexane, to completely remove any remaining ethanol from the column.

The resolubilized carotene extract is then applied to the column. The extract is washed through the column, typically using the same non-polar solvent as that in which it is dissolved, preferably hexane. Fractions containing the main band of orange-red carotene are then collected and the solvent removed, typically by evaporation and preferably in vacuo. The fraction then contains the high purity natural beta-carotene. By "high purity natural beta-carotene" as used herein is meant a composition which comprises from 30–60% all-trans-beta-carotene, 40–70% 9-cis-beta-carotene, up to a maximum of about 10% alpha-carotene, and up to no more than about 6% of other mono-cis and di-cis beta-carotene isomers combined. A typical preparation of high purity natural beta-carotene of the invention comprises 50% 9-cis-beta-carotene, 40% all-trans-beta-carotene, 5% alpha carotene, 2% other carotenoids, and 3% other cis-beta-carotene isomers.

After elution of the beta-carotene fraction from the column, elution with the same solvent is continued and subsequent fractions immediately following the main color band are collected, with another four to five column volumes being collected to remove virtually all of the pale yellow remaining carotenoids, including some beta-carotene. This is useful as a pro-vitamin supplement or as a natural coloring agent.

Periodically the column may be cleansed to remove any more polar carotenoids, plant lipids and chlorophyll from the column, typically by back-washing with a polar solvent such as acetone and/or ethanol. This wash is further processed by evaporation to recover solvent. Solids may be discarded or used in animal feed or as a health food. The column is then washed with 40% ethanol/non-polar solvent, followed by pure non-polar solvent as described above to restore it for further carotene purification. Periodically the build-up of green pigment and algal lipids cannot be eluted and the column may need to be repacked with fresh alumina as described above.

The natural high purity beta carotene preparation prepared as above may be used to produce compositions which comprise even further more highly purified 9-cis isomer beta-carotene. By "high purity natural 9-cis beta-carotene" as used herein is meant a mixture of alpha- and beta-carotenes derived from a plant source which comprises greater than 60% 9-cis-beta-carotene. Preferably the natural 9-cis-beta-carotene comprises at least 70% of the composition, more preferably at least about 80%, and most preferably 90% or more. Typically the ratio of 9-cis-beta-carotene to all-trans-beta-carotene will be greater than or equal to 3.0:1, preferably at least about 5.0:1.

The high-purity natural 9-cis-beta-carotene is produced by dissolving the high purity beta-carotene preparation in the minimal amount of warm (typically 40°-50° C.) non-polar solvent needed to solubilize the beta-carotene. A variety of non-polar solvents may be used, such as, for example, hexane, cyclohexane, pentane, heptane, octane, petroleum ethers, but preferably hexane. This solution is chilled, typically to about $-20°$ C., to cause the preferential crystallization of the all-trans isomer of beta-carotene. The crystals are then separated from the supernatant solution by any of the usual separation methods, e.g., filtration, centrifugation, decanting, etc. The remaining supernatant solution is then evaporated to remove the solvent, leaving a carotene preparation which comprises highly purified 9-cis-beta-carotene isomer. The final preparations will be substantially free of the organic solvent. By substantially free is meant that the preparation will contain no or little trace of organic solvent, and in any event will not exceed that amount permitted by regulatory agencies for administration to humans. To remove additional all-trans beta-carotene and produce a more highly purified 9-cis-beta carotene preparation, the supernatant solution containing the 9-cis-isomer can be re-evaporated, re-dissolved in a minimal amount of solvent as above, and re-crystallized by chilling.

The resulting all-trans beta-carotene by-product is typically 75% or more pure, and can be used for a variety of purposes, such as, for example, a source of vitamin A, a natural coloring product, or as a disease preventative or treatment.

The compositions of high-purity natural beta-carotene and 9-cis beta-carotene find a wide variety of uses, including as pharmaceuticals and as dietary vitamin supplements.

Depending on the intended mode of administration and the intended use, the compositions may be in the form of solid, semi-solid or liquid dosage forms, such, for example, as tablets, capsules, pills, microbeads, beadlets, powders, granules, crystals, liquids, suspensions, liposomes, etc., preferably in unit-dosage forms suitable for administration of relatively precise dosages. The compositions may include a conventional pharmaceutical carrier or excipient and, in addition, may include other medicinal agents or vitamins, pharmaceutical agents, carriers, etc.

The high-purity natural beta-carotene and 9-cis beta-carotene of the invention may be administered in relatively large amounts without serious side effects, although indiscriminate use may produce yellowing of the skin. In cases where the compositions are administered to prevent the emergence of disease in subjects susceptible to certain types of neoplasia, cardiovascular disease, etc., or to those suffering from only mild or borderline disease, the dose may be adjusted accordingly to lower maintenance levels.

For solid compositions, as would be appropriate for oral administration, the high-purity natural beta-carotene and 9-cis beta-carotene can be provided separately or may be compounded with conventional nontoxic solid carriers such as, for example, pharmaceutical grades of mannitol, lactose, starch, magnesium stearate, talcum, cellulose, glucose, sucrose, magnesium carbonate, and the like. Such compositions take the form of solutions, suspensions, tablets, pills, capsules, powders, granules, crystals, sustained-release formulations, and the like, and may contain about 10-100% active ingredient, preferably about 25-90%.

Liquid pharmaceutically-administrable compositions can, for example, be prepared by dissolving the high-purity natural beta-carotene and/or 9-cis beta-carotene and optional pharmaceutical adjuvants in a carrier for suspending or dissolving, such as, for example, mineral or vegetable oil and the like, to thereby form a solution or suspension. The concentration of the high-purity natural beta-carotene or 9-cis beta-carotene in these formulations can vary widely, and will be selected primarily by intended use, viscosities, etc., in accordance with the particular mode of administration selected.

As a dietary supplement the high-purity natural beta-carotene or 9-cis beta-carotene may be supplied as an oil, suspended in a capsule, beadlets, etc. or incorporated directly into foodstuffs as a convenient means of administration.

If desired, the pharmaceutical composition to be administered may also contain minor amounts of nontoxic auxiliary substances such as anti-oxidants, e.g., vitamin E (tocopherol), BHA, BHT, pH buffering agents and the like, for example, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Science, 17th ed., Mack Publishing Company, Easton, Pa. (1985), which is incorporated herein by reference. The composition or formulation to be administered will, in any event, contain a quantity of the high-purity natural beta-carotene and/or 9-cis beta-carotene in an amount effective to alleviate or ameliorate the symptoms of disease or inhibit their emergence in the subject.

The purified beta carotene compositions of the invention may be administered for a variety of therapeutic or prophylactic uses to humans or in veterinary applications. The compositions may be used as a vitamin preparation, alone or in conjunction with other vitamins, to supplement dietary intake of vitamin A and thus to treat or prevent conditions associated with vitamin A insufficiency. As beta-carotene, and particularly 9-cis beta-carotene, are anti-oxidants which can function in lipid environments at the low partial pressures of oxygen found in animal and human tissues, the compositions of the invention can also be used in prevention or treatment of a variety of diseases or pathological conditions associated with free radicals and lipid auto-oxidation.

In other uses the high-purity natural beta-carotene or 9-cis beta-carotene are administered therapeutically or prophylactically for a variety of cancers, particularly epithelial cell cancers. Beta-carotene preparations have shown significant protection against various tumors in animals. Among the animal models of cancer which established a protective or other beneficial effect of beta-carotene are skin cancers, including those induced by ultraviolet light (Epstein, *Photochem. Photobiol.* 25: 211 (1977), and Mathews-Roth, in Current Chemotherapy and Infectious Diseases, eds. Nelson and Grassi, Amer. Soc. Microbiol., Wash. D.C., p. 1503 (1980)), breast cancers (Santamaria et al., *Med. Biol. Environ.* 12:533 (1984)), fibrosarcomas (Combs et al., *Nutr. Cancer* 12:371 (1989)), epidermoid carcinomas (Shklar et al., *Nutr. Cancer* 12:321 (1989)), gastric cancer (Santamaria et al., *J. Nutr. Growth Cancer.* 4:175 (1987)), colon cancer (Santamaria et al., *Prev. Med.* 18:603 (1989)), exocrine pancreas neoplasias (Wouterson et al., *Cancer Lett.* 42:79 (1988)), bladder cancer (Mathews-Roth et al., *Oncology* 48:177 (1991)), and virus induced cancer (Seifter et al., *J. Natl. Can. Inst.* 78:1211 (1982)).

Accordingly, the beta-carotene and/or 9-cis beta-carotene preparations of the invention are indicated for use in therapeutic methods for a variety of cancers, including in humans. Beta-carotene preparations have been shown to be useful in treating, inhibiting or otherwise preventing tumors in humans, including lung cancers, such as squamous cell carcinoma, cancers of the gastrointestinal tract, e.g., mouth (Stich et al., *Intl. J. Cancer* 42:195 (1988) and Stich et al., in *Carotenoids: Chemistry and Biology*, eds. Krinsky et al., Plenum Press, p. 313 (1990)), pharynx, larynx (Mackerras et al., *Amer. J. Epidemiol.* 123: 980 (1988)), esophagus, stomach Graham et al., *Nutr. Cancer* 13: 19 (1990)), colon (Santamaria et al., *Prev. Med* 18:603 (1989), Temple et al., *J. Natl. Cancer Inst.* 78:1211 (1987) and Graham et al., *J. Natl. Cancer Inst.* 61:709 (1978)), rectum, bladder (Comstock et al., *Amer. J. Clin. Nutr.* 53:260s (1991), Tyler et al., *Eur. J. Surg. Oncol.* 12: 35 (1986), and Mathews-Roth et al., *Oncology* 48: 177 (1991)) and cervix (Palan et al., *Amer. J. Obstet. Gynecol.* 161: 1649 (1989). Beta-carotene has also been shown efficacious in preventing or inhibiting skin cancers such as melanoma (Comstock et al., supra) and epidermoid cancers of the head and neck (Shklar et al., *Nutr. Cancer* 12:321 (1989)). Carcinomas of the secretory glands, e.g., pancreas (Wouterson et al., *Cancer Lett.* 42: 79 (1988)), and breast (Basu, *J. Amer. Coll. Nutr.* 6: 451 (1987) and Santamaria et al., *Med. Biol. Environ.* 12: 533 (1984)), and mucosal dysplasias of the oral cavity, oropharynx and tongue (Malaker et al., *Clin. Invest. Med.* 10: B113 (1987)) have also reportedly been treated by the beta-carotenes. Each of the foregoing publications is incorporated by reference herein in its entirety.

Thus, the highly pure beta-carotene and/or 9-cis beta-carotene preparations of the invention are particularly useful in therapy or prevention of tumors which have been shown to be at least partially responsive to less pure preparations of beta-carotene. Because the 9-cis isomer is believed to be an effective anti-oxidant compared to other isomers of beta-carotene and may be better absorbed, preparations of this isomer are particularly preferred in the treatment or prevention of these tumors.

The high-purity natural beta-carotene and/or 9-cis beta-carotene compositions can also be applied to the skin or other tissues to diminish the effects of premature aging, e.g., damage to proteins and collagen tissue induced by exposure to ultraviolet radiation, such as with sunlight. Topical application of the beta-carotene preparations to the skin may be in the form of cremes, ointments, liquids and the like, or incorporated into cosmetics and toiletries.

Risk of cardiovascular disease, e.g., cardiac arrhythmias, myocardial infarctions, angina pectoris (Riemersma et al., *Lancet* i:337 (1991)), and stroke can also be diminished by the high-purity natural beta-carotene or 9-cis beta-carotene compositions of the invention.

Other indications for the high-purity beta-carotene preparations of the invention include those which have bee reported to benefit from treatment with less pure or synthetic beta-carotene preparations, such as Duchenne's muscular dystrophy ((Patsch et al., *Clin. Res.* 33: 441A (1985)) and cataract (Jacques et al., *Am. J. Clin. Nutr.* 53:352S (1991)). Beta-carotene has also been reported to enhance T and B lymphocyte proliferative responses (Bendich et al., *J. Nutr.* 116:2254 (1986)), such as increased T cell effector functions, including cytotoxic T cells, NK cells (Prabhala et al., *Clin. Res.* 36:142A (1988)), production of interleukins, to enhance anti-tumor immunity (Tomita et al., *J. Natl. Can. Inst.* 78:679 (1987)), and to protect polymorphonuclear cells from damage by free radicals during destruction of bacteria (Anderson and Theron, *World Rev. Nutr. Diet.* (1989)).

The synthetic preparations of beta-carotene contain only the all-trans form, whereas natural carotene from green plant tissues contain a mixture of isomers, and the compositions of the present invention are especially high in the 9-cis isomer, which is believed to be a better anti-oxidant than the synthetic all-trans isomer. Moreover, beta-carotene from natural sources has been reported to be absorbed at least ten-fold greater from the gastrointestinal tract than the all-trans form. Ben-Amotz et al., *J. Nutr.* 119:1013 (1989).

The pharmaceutical compositions ar intended for oral, local, topical or parenteral (i.e., intravenously, subcutaneously, or intramuscularly) administration for prophylactic and/or therapeutic treatment. Preferably, the pharmaceutical compositions are administered orally. As mentioned above, the 9-cis isomer of beta-carotene is a better anti-oxidant and is better absorbed than all-trans beta-carotene. These compositions may be sterilized by conventional, well known sterilization techniques. The compositions may contain pharmaceutically acceptable auxiliary substances as required to approximate physiological conditions and as necessary to prepare compositions for convenient administration, such an pH adjusting and buffering agents, and delivery vehicles, for example, vegetable or mineral oil. Actual methods for preparing pharmaceutically administrable compounds will be known or apparent to those skilled in the art and are described in detail in, for example, Remington's Pharmaceutical Science, supra.

Compositions of the invention are administered to a host already suffering from a neoplasia or cardiovascular disease, as described above, in an amount sufficient to cure or at least partially inhibit the disease and its complications. An amount adequate to accomplish this is defined as a "therapeutically effective dose." Amounts effective for this use will depend on the severity of the disease and the weight and general state of the patient being treated, but generally range from about 5 mg to about 2,000 mg per day of high-purity natural beta-carotene or 9-cis beta-carotene per day, with dosages of from about 10 mg to about 500 mg per day being more commonly used. Maintenance dosages over a prolonged period of time may be adjusted as necessary. It must be kept in mind that the compositions of the present invention may be employed in serious disease states, that is, life-threatening or potentially life threatening situations. In such cases, it is possible and may be felt desirable by the treating physician to administer substantial excesses of these compositions. For veterinary uses higher levels may be administered as necessary.

Determining actual amounts of the high-purity natural beta-carotene and/or 9-cis beta-carotene necessary to inhibit or treat a particular disease, such as neoplasias, cardiovascular disease, immune disorders, etc. as described above will be through standard empirical methods which are well known in the art.

In prophylactic applications compositions containing the high-purity natural beta-carotene and/or 9-cis beta-carotene are administered to a host susceptible to or otherwise at risk of diseases associated with vitamin A deficiency or oxidation-associated diseases to enhance the patient's own capabilities against the disease. Such an amount is defined to be a "prophylactically effective dose." In this use, the precise amounts again depend on the patient's state of health and weight, but generally range from about 3 mg to about 500 mg per day, more commonly from about 10 mg to about 30 mg per day. Single or multiple administrations of the compositions can be carried out with the dose levels and pattern being selected by the treating physician or health care specialist.

The compositions of the invention, including pharmaceutical compositions, may be administered alone or as adjunct therapy or prophylaxis. The compositions may be administered with, e.g., other anti-cancer or anti-cardiovascular disease therapies, or as components of dietary regimens.

The following examples are provided by way of illustration, not limitation.

EXAMPLE I

Preparation of High Purity Natural Beta-Carotene

This Example describes the preparation of high purity beta carotene.

*Dunaliella salina* was raised in cultivation tanks comprised of a paddlewheel system in 4'×10'tanks, with a 4"water level. The culture medium was 2.5 M salt water, with 0.2 mM phosphate, 5 mM $HCO_3$, 1 mM $NO_3$, iron and trace minerals and maintained at a temperature of about 35° C. under controlled lighting conditions (six 1000 watt halide lights at 10-12"from surface). Nitrate limitation was used to induce carotene production. When the culture reached a density of 0.25 grams dry wt/l, algae were harvested from the cultivation tanks and flocculated using alum to form an algal slurry. The slurry was mixed with diatomaceous earth and vacuum filtered to remove most of the water, then treated with hot (60° C.) water and then made as dry as possible with vacuum. The resulting cake was then extracted with hexane to remove the crude carotene preparation.

The hexane solvent was then removed by evaporation under vacuum at 40°-50° C. and the crude extract was re-dissolved in the minimum amount of hexane possible. This solution was then applied to a 3"×12"chromatographic column prepared as follows: Activated alumina (aluminum oxide) of a chromatographic grade (Aldrich Chemical CO., Brockman grade I, acidic, about 150 mesh), was deactivated by suspending it overnight in 2 volumes aqueous ethanol at a mixture of 70 parts ethyl alcohol to 30 parts water. The deactivated alumina was then packed into the column as a slurry in the water/alcohol mixture. The slurry was then washed well with four volumes of absolute ethanol to remove the water, followed by a wash with two column volumes of 40% ethanol in hexane. The column was then washed with hexane for at least five to six column volumes to completely remove any remaining ethanol.

The crude carotene extract was then applied to the column in about 100 ml hexane and washed through the column with hexane. A fraction of 300 ml containing the main band of orange-red carotene was collected and the solvent removed by vacuum evaporation. At this stage the beta-carotene was approximately 90-95% purified, as shown in a representative chromatogram of FIG. 1 using a Supelco column which does not resolve the various isomers of beta-carotene. A similar preparation on a Vydac column, which does resolve the beta-carotene isomers, shows the beta-carotene is comprised of approximately 55% 9-cis isomer and about 45% all-trans isomer (FIG. 2A).

Elution with hexane was continued into a different container immediately after the main color band, with two liters being collected to remove virtually all of the pale yellow material, primarily beta-carotene with other carotenes and carotenoids, which was kept as a separate by-product of 50-80% pure beta-carotene.

Periodically, the column was cleansed by back-washing with a polar solvent, typically acetone or ethanol, to remove oxygenated carotenoids, plant neutral lipids and chlorophyll from the top of the column. This material may contain small amounts of astaxanthin and/or canthaxanthin which are valuable in fish feed as colorants for farmed salmon and trout. The column was washed as before with 40% ethanol/hexane solvent and pure hexane to restore it for further carotene purification. Periodically, as needed by the build up of chlorophyll and other lipids which could not be eluted as above, the top 2"-3"of the column was re-packed with fresh alumina.

Figure 1:
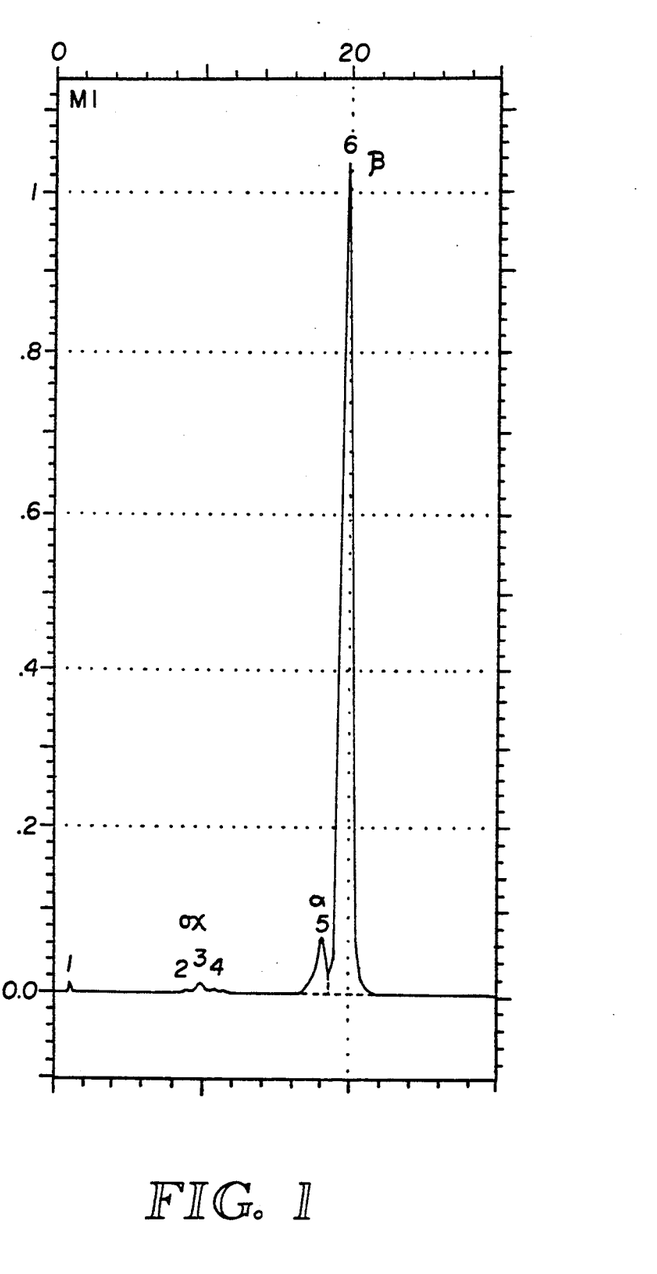
FIG. 1 is a chromatogram depicting highly enriched natural beta-carotene after initial fractionation.
Figure 2A:
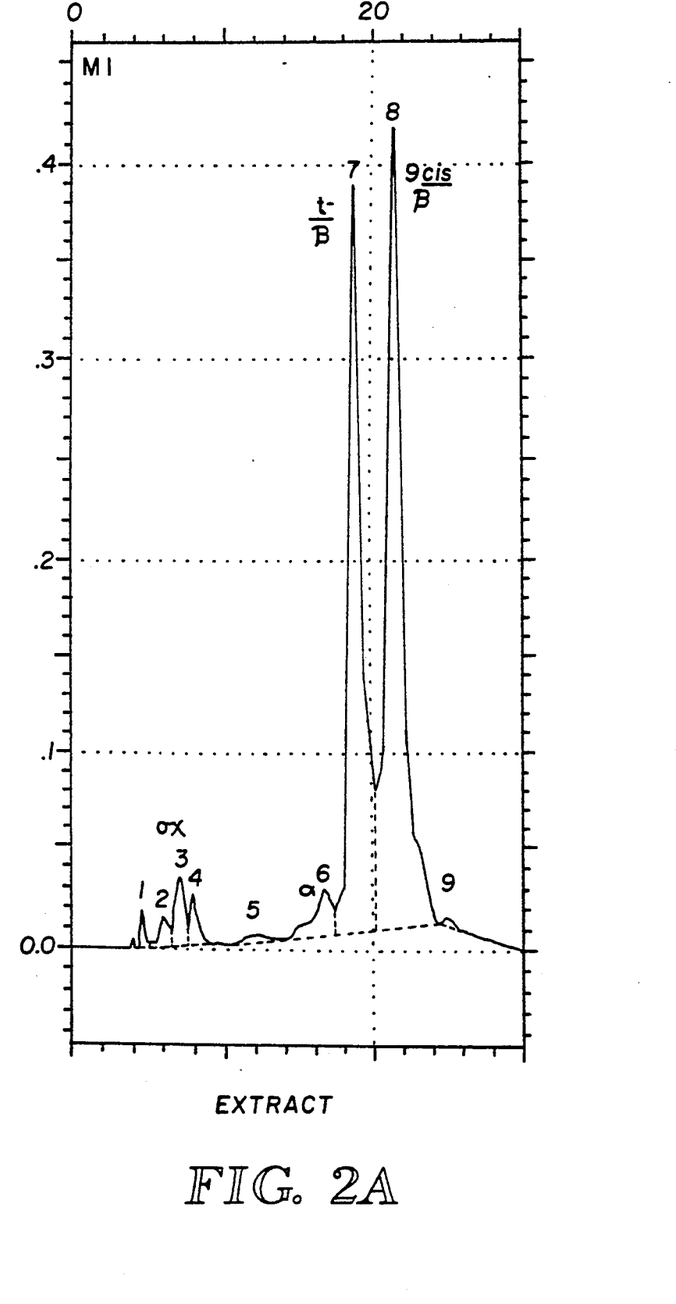
FIG. 2A is a chromatogram which shows the same material as in FIG. 1, but with the β-carotene isomers resolved by use of a Vydac column.

The resulting preparation of high purity beta-carotene was evaporated to remove solvent and yielded about 95% beta carotene and 5% alpha-carotene, as shown in FIG. 1. Purity was confirmed by thin layer chromatography and HPLC.

EXAMPLE II

Production of High Purity 9-Cis Beta-Carotene

This Example describes the production of beta-carotene enriched in the 9-cis isomer from the high purity beta-carotene prepared as described in Example I.

Figure 2B:
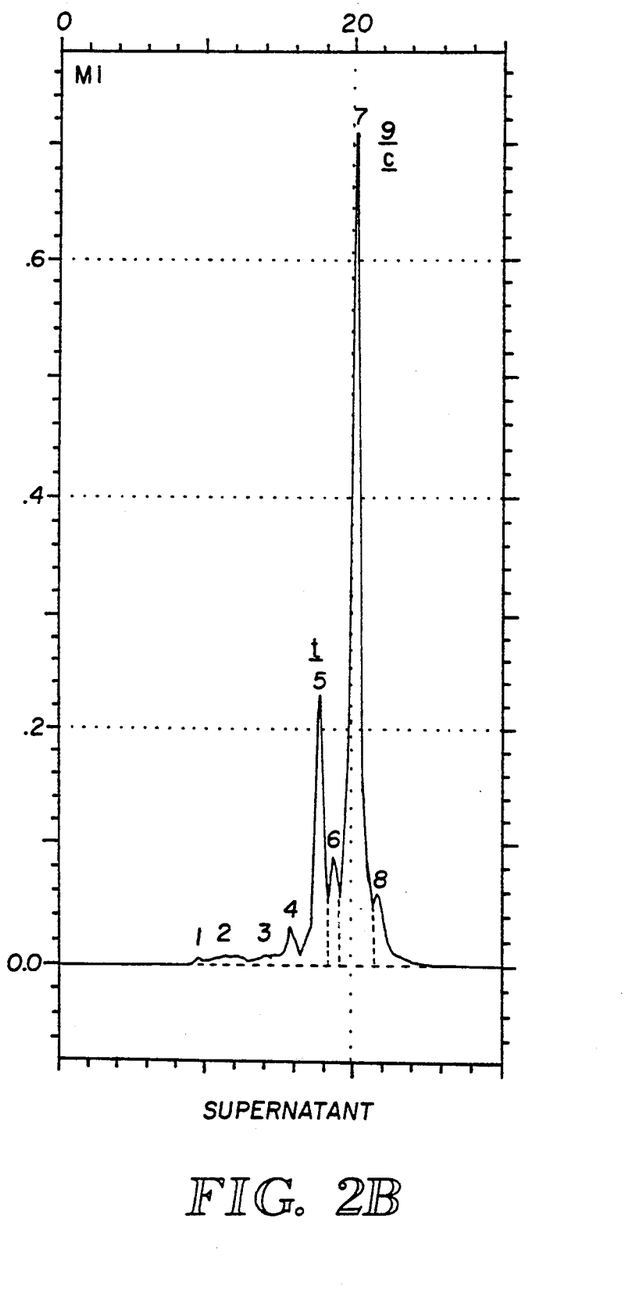
FIGS. 2B and 2C are chromatograms from subsequent purification steps to produce preparations enriched for the 9-cis isomer and all-trans isomer, respectively, of beta-carotene.
Figure 2C:
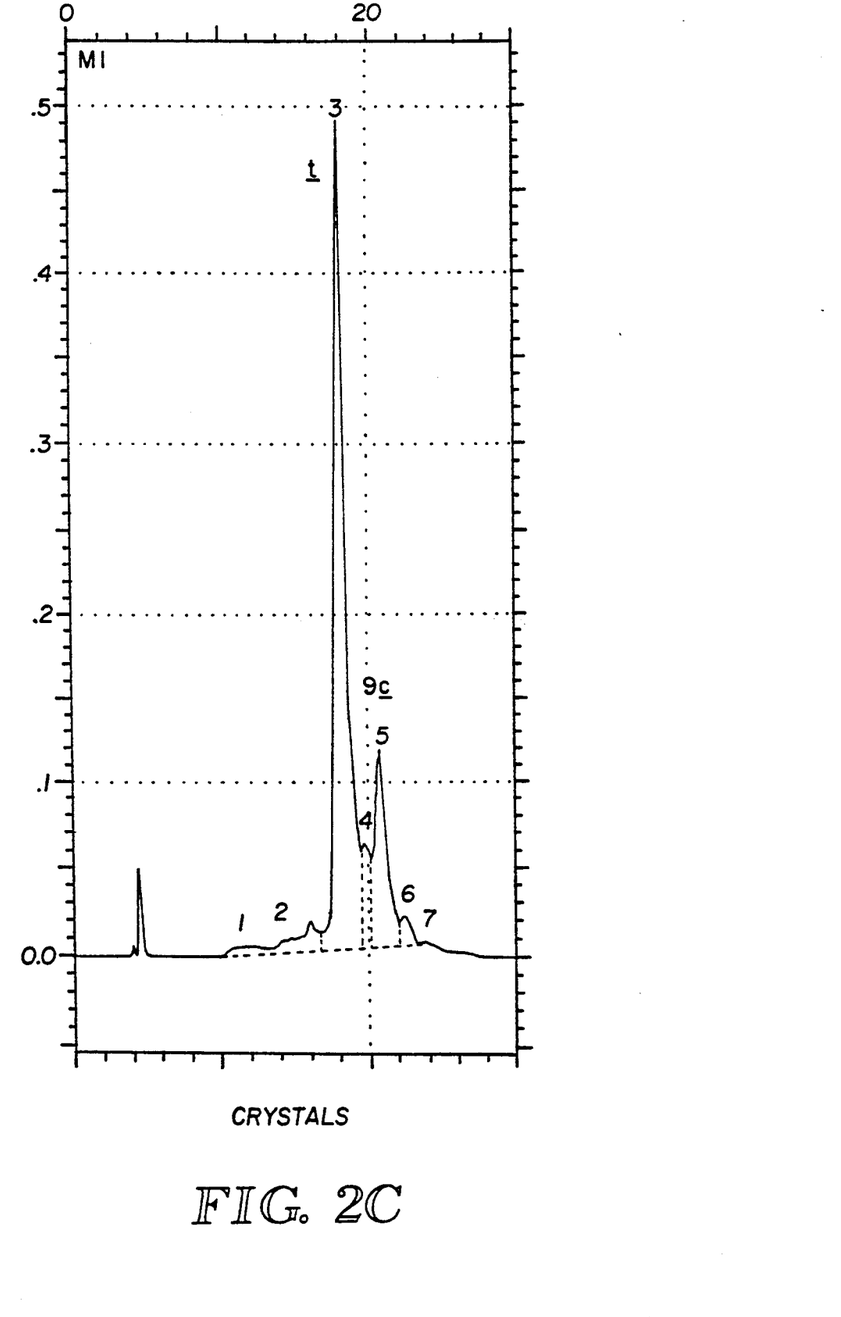

High purity beta-carotene from Example I was dissolved in a minimal amount of warm (about 40°-50° C.) hexane to achieve saturation. The solution was then chilled, typically to about −20° C., which caused the preferential crystallization of the trans-isomer of beta-carotene. The crystals were then separated from the supernatant solution by filtration through a hydrophobic 0.22 $\mu$ nylon membrane filter (Micron Separations, Inc., Cambridge, MA). Chromatograms of representative preparations of the supernatant enriched in the 9-cis isomer (approximately 75-80% 9-cis and 15-20% all-trans) and of the crystals containing the all-trans isomer (approximately 80-85% all-trans and 10-15% 9-cis) are shown in FIGS. 2B and 2C, respectively.

The supernatant solution was then evaporated to dryness under vacuum, at about 40° C. and under low light (as with all of the purification steps described herein) to remove the hexane, leaving a carotene preparation which was substantially enriched in the 9-cis isomer. Typical yield of the 9-cis isomer from these preparations was approximately 2-3 grams. Experience with these purification procedures indicate they can readily be scaled up to pilot and production levels.

EXAMPLE III

Capsule Formulation

This Example describes formulation of a dietary composition containing beta-carotene of the invention which is intended for oral administration in capsule form.

| Ingredients | Amount |
| --- | --- |
| High Purity Beta-Carotene | 30 mgs |
| Vitamin E | 400 I.U. |
| Vitamin C | 500 mgs |

The above ingredients are combined and placed into a gelatin capsule suitable for administration to humans.

It is evident from the above that the subject invention provides high-purity natural beta-carotene and 9-cis beta-carotene which find use as dietary supplements for humans and other animals, and in the therapy of a number of diseases, including certain neoplasias, and in the prevention of other diseases, such as cardiovascular disease. Furthermore, the invention provides economical methods to prepare the high-purity natural beta-carotene and 9-cis beta-carotene from plant matter, conveniently from large scale alga propagation.

All publications and patents mentioned in this specification are indicative of the level of skill of those skilled in the art to which this invention pertains. All publications and patents are herein incorporated by reference to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for purifying beta-carotene from plants, which comprises:
   extracting the plant with a solvent to produce a crude mixture of carotenes in the extract;
   removing the solvent from the extract and resuspending the extract in a non-polar solvent;
   chromatographing the extract on a column of deactivated alumina; and
   collecting fractions from the column which contain the purified beta-carotene.

2. The method according to claim 1, wherein the plant is an alga.

3. The method according to claim 2, wherein the alga is a Dunaliella species.

4. The method according to claim 1, wherein the extraction solvent is an organic solvent.

5. The method according to claim 4, wherein the extracting organic solvent is selected from hexanes, pentanes, heptanes, octanes, petroleum ethers, cyclohexane, ethyl acetate, ethanol and mixtures thereof.

6. The method according to claim 1, wherein the non-polar solvent is a pentane, hexane, heptane, octane, or petroleum ether.

7. The method according to claim 1, wherein the alumina is deactivated with aqueous ethanol.

8. A composition prepared according to the method of claim 1 which comprises substantially purified naturally occurring beta-carotene isomers, in relative amounts of at least 40% 9-cis beta-carotene and less than about 50% all-trans beta-carotene, and substantially free of organic solvent.

9. The method according to claim 1, further comprising the steps of:
   dissolving the purified beta-carotene in a non-polar solvent at about 35°-60° C. to form a saturated solution;
   chilling the solution to about 0° C. to −25° C. to crystallize all-trans beta-carotene and separating the solution from the crystallized all-trans beta-carotene; and
   removing the solvent from the solution to yield a preparation enriched in 9-cis beta-carotene.

10. The method according to claim 9, wherein the purified beta-carotene is dissolved in hexane.

11. The method according to claim 9, wherein the crystallized all-trans beta-carotene is separated from the solution by filtration, centrifugation or decanting.

12. A composition produced by the method of claim 9, which comprises substantially purified naturally occurring beta-carotene isomers including at least 75% 9-cis beta-carotene, and is substantially free of organic solvent.

13. The method according to claim 9, further comprising repeating with the preparation enriched in 9-cis beta-carotene, the steps of
   dissolving in non-polar solvent at about 35°-60° C.;
   chilling the solution to crystallize the all-trans beta-carotene and separating the solution from the crystals; and
   removing the solvent to yield a preparation further enriched in 9-cis beta-carotene.

14. A composition produced by the method of claim 13, which comprises substantially purified naturally occurring beta-carotene isomers including at least 75% 9-cis beta-carotene, and is substantially free of organic solvent.

15. A composition which comprises substantially purified naturally occurring beta-carotene, isomers, in relative amounts of at least 40% 9-cis beta-carotene and less than about 50% all-trans beta-carotene, and substantially free of organic solvent.

16. The composition according to claim 15, formulated as a tablet, capsule or microbeadlet or oil for use as a dietary supplement.

17. The composition according to claim 15, further comprising less than 10% alpha-carotene.

18. The composition according to claim 17, further comprising 2% or less of carotenoids other than alpha- and beta-carotene, and 5% or less of other cis beta-carotene isomers.

19. The composition according to claim 15, comprising at least about 60% 9-cis beta-carotene and less than 25% all-trans beta-carotene.

20. The composition according to claim 19, further comprising a pharmaceutically acceptable carrier.

21. The composition according to claim 19, formulated as a tablet, capsule or microbeadlet or oil for use as a dietary supplement.

22. The composition according to claim 19, comprising 75% or more 9-cis beta-carotene.

23. The composition according to claim 22, further comprising a pharmaceutically acceptable carrier.

24. The composition according to claim 22, formulated as a tablet, capsule or microbeadlet or oil for use as a dietary supplement.

25. A method for inhibiting a tumor in a host, which comprises administering to the host a tumor-inhibiting amount of a pharmaceutical composition which comprises substantially purified naturally occurring beta-carotene isomers, in relative amounts of at least 40% 9-cis beta-carotene and less than about 50% all-trans beta-carotene.

26. The method of claim 25, wherein the pharmaceutical composition administered to the host comprises at least about 75% 9-cis beta-carotene.

* * * * *